(12) United States Patent
Welsch et al.

(10) Patent No.: US 10,016,556 B2
(45) Date of Patent: Jul. 10, 2018

(54) ROTATABLE ELECTRICAL CONNECTORS

(71) Applicant: Smiths Medical ASD, Inc., Rockland, MA (US)

(72) Inventors: Michael Welsch, Stillwater, MN (US); Grant Adams, Coon Rapids, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 0 days.

(21) Appl. No.: 14/787,447

(22) PCT Filed: Apr. 29, 2014

(86) PCT No.: PCT/US2014/035878
§ 371 (c)(1),
(2) Date: Oct. 27, 2015

(87) PCT Pub. No.: WO2014/179317
PCT Pub. Date: Nov. 6, 2014

(65) Prior Publication Data
US 2016/0074574 A1    Mar. 17, 2016

Related U.S. Application Data

(60) Provisional application No. 61/817,067, filed on Apr. 29, 2013.

(51) Int. Cl.
*A61M 5/145* (2006.01)
*H01R 35/04* (2006.01)
*H01R 13/66* (2006.01)

(52) U.S. Cl.
CPC ......... *A61M 5/1452* (2013.01); *H01R 13/665* (2013.01); *H01R 35/04* (2013.01); *H01R 2201/12* (2013.01)

(58) Field of Classification Search
CPC ...... H01R 12/714; H01R 13/24; H01R 12/79; H01R 12/88; H01R 13/6205;
(Continued)

(56) References Cited

U.S. PATENT DOCUMENTS 4,526,432 A * 7/1985 Cronin ................. H01R 12/777
439/320
4,533,796 A   8/1985 Engelmore
(Continued)

FOREIGN PATENT DOCUMENTS

AT   323334 E   4/2006
CA   1210105 A1 8/1986
(Continued)

OTHER PUBLICATIONS

Extended European Search Report, U.S. Appl. No. 14/792,313, dated Dec. 6, 2016, 9 pages.
(Continued)

*Primary Examiner* — Truc Nguyen
(74) *Attorney, Agent, or Firm* — Patterson Thuente Pederson, P.A.

(57) ABSTRACT

A rotatable electrical connector can include a base housing having a bottom surface, a top housing that is rotatably engaged with the base housing, and a plurality of contact pads that are arranged radially within the base housing. The contact pads each have a top surface and a bottom surface. A plurality of signal pins are individually associated with the plurality of contact pads; and each of the signal pins correspondingly project outwardly from the bottom surface of an associated contact pad and outwardly from the bottom surface of the base housing. A center ground pad, having a top surface and a bottom surface, is provided within the base housing. A ground pin projects outwardly from the bottom surface of the center ground pad and outwardly from the
(Continued)

bottom surface of the base housing. A plurality of conductors is arranged radially within the top housing. The conductors individually correspond to the plurality of contact pads within the base housing. Each of the conductors has (i) a bottom surface that is capable of being in rotatable contact with the top surface of each of the contact pads and (ii) a top surface that projects outwardly from the top housing. A ground conductor is centrally located within the top housing and is surrounded by the plurality of conductors. The ground conductor has a bottom surface that is in rotatable contact with the top surface of the center ground pad in the base housing, and a top surface that projects outwardly from the top housing.

8 Claims, 5 Drawing Sheets

(58) Field of Classification Search
CPC .. H01R 2201/12; H01R 12/57; H01R 12/716; H01R 11/22; H01R 12/52; H01R 12/7082; H01R 13/2421; H01R 13/6599; H01R 2103/00
See application file for complete search history.

(56) References Cited

U.S. PATENT DOCUMENTS

| | | | | |
|---|---|---|---|---|
| 4,753,600 A * | 6/1988 | Williams | | H01R 39/64 439/22 |
| 4,773,866 A | 9/1988 | Basques | | |
| 4,870,311 A | 9/1989 | Chase et al. | | |
| 4,927,364 A | 5/1990 | Inui | | |
| 4,932,882 A | 6/1990 | Kang | | |
| 4,978,335 A | 12/1990 | Arthur, III | | |
| 5,082,448 A | 1/1992 | Kang | | |
| 5,124,608 A | 6/1992 | Lawrence et al. | | |
| 5,231,374 A | 7/1993 | Larsen et al. | | |
| 5,267,069 A | 11/1993 | Griffin et al. | | |
| 5,352,122 A | 10/1994 | Fong | | |
| 5,551,882 A * | 9/1996 | Whiteman, Jr. | | H01R 35/04 439/21 |
| 5,857,866 A * | 1/1999 | Felps | | H01R 13/08 439/289 |
| 5,984,687 A | 11/1999 | Schwarz | | |
| 6,634,888 B2 * | 10/2003 | Villain | | H01R 24/38 439/21 |
| 6,692,278 B2 | 2/2004 | Abadia et al. | | |
| 6,767,217 B2 | 7/2004 | Jacobson | | |
| 6,768,233 B2 | 7/2004 | Angerpointner | | |
| 6,994,557 B2 | 2/2006 | Huscher et al. | | |
| 7,002,269 B2 | 2/2006 | Angerpointer | | |
| 7,101,187 B1 | 9/2006 | Deconinck et al. | | |
| 7,125,257 B1 | 10/2006 | Liang | | |
| 7,192,303 B2 * | 3/2007 | Kohen | | F21V 21/03 439/135 |
| 7,654,976 B2 | 2/2010 | Peterson et al. | | |
| 7,967,773 B2 | 6/2011 | Amborn et al. | | |
| 8,030,891 B2 | 10/2011 | Welsch et al. | | |
| 8,182,461 B2 | 5/2012 | Pope et al. | | |
| 8,209,060 B2 | 6/2012 | Ledford | | |
| 8,331,106 B2 * | 12/2012 | Tang | | G06F 1/181 361/807 |
| 9,664,868 B2 * | 5/2017 | Logan, Jr. | | G02B 6/4293 |

| | | |
|---|---|---|
| 2002/0130568 A1 | 9/2002 | Angerpointner |
| 2003/0109149 A1 | 6/2003 | Masriera |
| 2003/0124891 A1 | 7/2003 | Huscher et al. |
| 2003/0176082 A1 | 9/2003 | Jacobson |
| 2004/0164642 A1 | 8/2004 | Angerpointner |
| 2005/0033223 A1 | 2/2005 | Herrera |
| 2006/0003604 A1 | 1/2006 | Angerpointner |
| 2009/0221918 A1 | 9/2009 | Harshrnan et al. |
| 2010/0049164 A1 | 2/2010 | Estes |
| 2010/0173515 A1 | 7/2010 | Dickenson |
| 2010/0285687 A1 | 11/2010 | Wadsworth |
| 2011/0133946 A1 | 6/2011 | Kopp et al. |
| 2011/0137239 A1 | 6/2011 | Debelser et al. |
| 2013/0078867 A1 | 3/2013 | Chongyu et al. |

FOREIGN PATENT DOCUMENTS

| | | |
|---|---|---|
| CN | 2718860 Y | 8/2005 |
| CN | 2857279 Y | 1/2007 |
| CN | 101095268 A | 12/2007 |
| CN | 101909691 A | 12/2010 |
| DE | 20115043 U1 | 3/2002 |
| DE | 10112895 A1 | 9/2002 |
| DE | 10162127 A1 | 7/2003 |
| DE | 20122112 U1 | 5/2004 |
| DE | 10112895 B4 | 9/2011 |
| EP | 0169890 A1 | 2/1986 |
| EP | 1269604 A1 | 1/2003 |
| EP | 1324435 A2 | 7/2003 |
| EP | 1324435 A3 | 5/2004 |
| EP | 1324435 B1 | 4/2006 |
| EP | 1269604 B1 | 11/2011 |
| FR | 2642909 A1 | 8/1990 |
| FR | 2819943 A1 | 7/2002 |
| FR | 2819943 B1 | 2/2003 |
| GB | 1526900 A | 10/1978 |
| JP | S5654590 U | 5/1981 |
| JP | H 0214186 U | 11/1990 |
| JP | 2004517460 T2 | 6/2004 |
| JP | 2007-179860 A | 7/2007 |
| JP | 4041401 B | 1/2008 |
| JP | 2011 194155 A | 10/2011 |
| KR | 20000031973 A | 6/2000 |
| MX | PA02009397 A1 | 2/2003 |
| WO | WO 8503388 A1 | 8/1985 |
| WO | WO 9306573 A1 | 4/1993 |
| WO | WO 02060038 A1 | 8/2002 |
| WO | WO 2012/009820 A1 | 1/2012 |

OTHER PUBLICATIONS

International Preliminary Report on Patentability, International Application No. PCT/US2014/035878. dated Nov. 12, 2015, 8 pages.
Australian Examination Report No. 1 for Australian Application No. 2014260087 dated Mar. 3, 2017.
PCT International Search Report for PCT/US/2014/035878, dated Sep. 2, 2014, 3 pgs.
Notice of Grant dated Aug. 29, 2017 for Chinese Application No. 201480024245.6, 2 pages.
Office Action dated Jan. 22, 2017 for Chinese Application No. 201480024245.6, 5 pages.
Communication dated Mar. 2, 2018 for EP Application No. 14792310.0, 8 pages.
Office Action dated Dec. 18, 2017 for Japanese Application No. 2016-511802, 3 pages.

* cited by examiner

| PIN | STATE (FIG.2) | STATE (FIG.2D) | STATE (NOT ILLUSTR.) | STATE (NOT ILLUSTR.) | STATE (NOT ILLUSTR.) | STATE (NOT ILLUSTR.) | STATE (FIG.2) | STATE 'ETC.' |
|---|---|---|---|---|---|---|---|---|
| 212A | SWITCH NORMALLY OPEN | RED LED POWER | RDC POWER | SWITCH NORMALLY CLOSED (INDEX) | BLUE LED POWER | SWITCH NORMALLY OPEN | SWITCH NORMALLY OPEN | |
| 212B | BLUE LED POWER | SWITCH NORMALLY OPEN | RED LED POWER | RDC POWER | SWITCH NORMALLY CLOSED (INDEX) | BLUE LED POWER | BLUE LED POWER | |
| 212C | SWITCH NORMALLY CLOSED (INDEX) | BLUE LED POWER | SWITCH NORMALLY OPEN | RED LED POWER | RDC POWER | SWITCH NORMALLY CLOSED (INDEX) | SWITCH NORMALLY CLOSED (INDEX) | |
| 212D | RDC POWER | SWITCH NORMALLY CLOSED (INDEX) | BLUE LED POWER | SWITCH NORMALLY OPEN | RED LED POWER | RDC POWER | RDC POWER | |
| 212E | RED LED POWER | RDC POWER | SWITCH NORMALLY CLOSED (INDEX) | BLUE LED POWER | SWITCH NORMALLY OPEN | RED LED POWER | RED LED POWER | |
| 212G | GROUND | GROUND | GROUND | GROUND | GROUND | GROUND | GROUND | |
| ROTATE → | (FIGS. 2B-C) | (NOT ILLUSTR.) | (NOT ILLUSTR.) | (NOT ILLUSTR.) | (NOT ILLUSTR.) | (NOT ILLUSTR.) | (FIGS. 2B-C) | 'ETC.' |

ROTATABLE ELECTRICAL CONNECTORS

RELATED APPLICATIONS

The present application is a National Phase entry of PCT Application No. PCT/US2014/035878, filed Apr. 29, 2014, which claims the benefit of U.S. Provisional Patent Application No. 61/817,067, filed Apr. 29, 2013, each of which is incorporated herein by reference in its entirety.

TECHNICAL FIELD

This disclosure relates generally to electrically-conductive connectors. More particularly, this disclosure relates to rotatable electrical connectors which may be used in, for example, medical infusion devices.

BACKGROUND

In the field of medical infusion devices including so-called "syringe pumps" and "ambulatory infusion pumps", typically a pre-filled medication syringe or reservoir is mechanically driven or controlled by a microprocessor to deliver a prescribed amount or dose of a drug or fluid at a controlled rate to a patient through an infusion line fluidly connected to the syringe or reservoir. Drugs or fluids delivered to a patient by way of syringe pumps and ambulatory infusion pumps can include, but are not limited to: therapeutic agents; nutrients; drugs; medicaments such as antibiotics, blood clotting agents, and analgesics; and other fluids. The devices can be used to introduce the drugs or fluids into patients' bodies utilizing any of several routes such as, for example, intravenously, subcutaneously, arterially, or epidurally.

Examples of syringe pumps and related components are disclosed in U.S. Pat. No. 4,978,335 titled "Infusion Pump with Bar Code Input to Computer," U.S. Pat. No. 8,182,461 titled "Syringe Pump Rapid Occlusion Detection System," and U.S. Pat. No. 8,209,060 titled "Updating Syringe Profiles for a Syringe Pump." As used throughout this disclosure, the term "syringe pump" is intended to generally pertain to any device which acts on a syringe to controllably force fluid outwardly therefrom. Examples of ambulatory infusion pumps and related components are disclosed in U.S. Pat. No. 7,654,976 titled "Drug Pump Systems and Methods," U.S. Pat. No. 8,030,891 titled "Ambulatory Medical Device with Electrical Isolation from Connected Peripheral Device," U.S. Pat. No. 7,967,773 titled "Two Piece Medication Cassette Closure Apparatus and Method," U.S. Pat. Applic. Pub. No. 2011/0133946 titled "Guided User Help System for an Ambulatory Infusion device," and U.S. Pat. Applic. Pub. No. 2011/0137239 titled "Advanced Step Therapy Delivery for an Ambulatory Infusion Pump and system." As used throughout this disclosure, the term "ambulatory infusion pump" is intended to generally pertain to any device which acts on a reservoir to controllably force fluid outwardly therefrom, or otherwise regulate a flow of fluid to a patient.

In use of medical infusion devices such as syringe pumps and ambulatory infusion pumps, it may be desirable or even necessary in particular circumstances to provide means for limited direct control of the devices by the patients themselves. Such functionality may be desirable when, for example, a patient is receiving a medication to alleviate pain and an attending physician or practitioner has deemed it permissible for the patient to control, within limits, how frequently the pain medication is administered and how much is delivered from the infusion device. However, infusion devices often have operational complexities that exceed the training or experience of typical patients; and controlled substances such as pain medications often have strict "hard" volume and frequency administration limits for overdose prevention and patient safety. Thus it is often desirable to employ an accessory known as a "remote dose cord" with an infusion device, for such "self-administration" of pain medication by and to the patient. A remote dose cord typically includes a hand-held controller, and an electrically-conductive, insulated electrical transmission cord or cable extending from the controller which terminates in an electrical connector that is configured for coupling to an electrical connection port of the infusion device. Remote dose cords usually are, by design, relatively easy to operate: the hand-held controllers typically have only one clearly marked button for the patient to push, and are ergonomically designed to accommodate use by patients having limited dexterity, motion, strength, or lack of visual acuity. Remote dose cords typically also indicate when a next dose is "available" or "unavailable" to the patient through use of a lighted or blinking light-emitting diode (LED), or other signaling means such as an audible beeper or a vibrating hand-held controller, or any combination of such signaling means, in cooperation with software with or for medical infusion devices.

The electrical connector, at the end of the remote dose cord opposite the hand-held controller, typically has a plurality of pins which engage corresponding sockets in an electrical connection port of the infusion device. The pins in the connector, when engaged in the sockets in the electrical connection port of the infusion device, provide electrical power and signal transfer capabilities between the remote dose cord and the infusion device. Accordingly when, for example, a patient pushes the button on the hand-held controller of the remote dose cord to receive a desired bolus of pain medication, a command signal responsively generated by circuitry within the controller is transmitted through the cord and connector and into the infusion device. The command signal is then processed by the infusion device for a determination of whether, for example, it is safe to deliver the requested pain medication to the patient.

Unfortunately, problems may arise in use of known electrical connectors that couple the remote dose cords to the infusion devices. Known electrical connectors may be subject to external forces that may compromise their structural integrity when the pins are engaged in the sockets of the infusion device. For example, a patient may mishandle a connector by trying to twist or rotate it while it is coupled to an electrical connection port in an infusion device; or the pins in the connector may be subject to a rotating or other deleterious force or load when, for example, the connector is inadvertently bumped or momentarily comes into contact with a stationary object such as a wall while the patient is walking with the device. Regardless of a particular instance of mishandling or external force, such electrical connectors and the cords from which they extend are intended to remain stationary and not twist with respect to the infusion device. Thus, such twisting motions or rotating forces can result in broken pins and other failures in remote dose cords and infusion devices.

It would therefore be useful and advantageous to provide rotatable electrical connectors with remote dose cords, which would not be adversely affected by twisting or rotating forces while coupled to electrical connection ports in infusion devices.

SUMMARY

This disclosure describes novel and inventive rotatable electrical connectors which may be used in, for example, medical infusion devices.

A rotatable electrical connector can include a base housing having a bottom surface, a top housing that is rotatably engaged with the base housing, and a plurality of contact pads that are arranged radially within the base housing. The contact pads each have a top surface and a bottom surface. A plurality of signal pins are individually associated with the plurality of contact pads; and each of the signal pins correspondingly project outwardly from the bottom surface of an associated contact pad and outwardly from the bottom surface of the base housing. A center ground pad, having a top surface and a bottom surface, is provided within the base housing. A ground pin projects outwardly from the bottom surface of the center ground pad and outwardly from the bottom surface of the base housing. A plurality of conductors is arranged radially within the top housing. The conductors individually correspond to the plurality of contact pads within the base housing. Each of the conductors has (i) a bottom surface that is capable of being in rotatable contact with the top surface of each of the contact pads and (ii) a top surface that projects outwardly from the top housing. A ground conductor is centrally located within the top housing and is surrounded by the plurality of conductors. The ground conductor has a bottom surface that is in rotatable contact with the top surface of the center ground pad in the base housing, and a top surface that projects outwardly from the top housing.

A medical infusion device can include a rotatable electrical connector as aforedescribed. A remote dose cord is connected to the plurality of conductors and the ground conductor of the rotatable electrical connector. An infusion pump has an electrical connection port; and the plurality of signal pins and the ground pin of the rotatable electrical connector are connected to the electrical connection port of the infusion pump.

The aforedescribed rotatable electrical connector can be characterized in that the top housing and the plurality of conductors rotate relative to the base housing and the plurality of signal pins; and a microcontroller remaps the pins according to rotation of the top housing with respect to one of the plurality of conductors that is electrically connected to the ground conductor. The aforedescribed rotatable electrical connector can be further characterized in that the plurality of signal pins is removably coupled to an infusion device.

In another embodiment, a rotatable electrical connector can include a base housing having a bottom surface, a top housing that is rotatably engaged with the base housing, and a plurality of contact pads that are arranged radially within the base housing. The contact pads each have a top surface and a bottom surface. A plurality of signal pins are individually associated with the plurality of contact pads; and each of the signal pins correspondingly project outwardly from the bottom surface of an associated contact pad and outwardly from the bottom surface of the base housing. A plurality of conductors is arranged radially within the top housing. The conductors individually correspond to the plurality of contact pads within the base housing. Each of the conductors has (i) a bottom surface that is capable of being in rotatable contact with the top surface of each of the contact pads and (ii) a top surface that projects outwardly from the top housing. A selected pair of the plurality of conductors is electrically connected to thereby create a rotational index among the remaining plurality of conductors.

A medical infusion device can include another embodiment of a rotatable electrical connector as aforedescribed. A remote dose cord is connected to the plurality of conductors of the rotatable electrical connector. An infusion pump has an electrical connection port; and the plurality of signal pins of the rotatable electrical connector are connected to the electrical connection port of the infusion pump.

The aforedescribed another embodiment of a rotatable electrical connector can be characterized in that the top housing and the plurality of conductors rotate relative to the base housing and the plurality of signal pins; and a microcontroller remaps the pins according to rotation of the top housing with respect to the selected pair of the plurality of conductors that are electrically connected to create the rotational index. The aforedescribed another embodiment of a rotatable electrical connector can be further characterized in that the plurality of signal pins is removably coupled to an infusion device.

BRIEF DESCRIPTION OF THE DRAWINGS

Rotatable electrical connectors are illustrated by way of example and not limitation in the figures of the accompanying drawings in which.

DETAILED DESCRIPTION

Rotatable electrical connectors described in greater detail by way of examples herein provide coupling of remote dose cords to medical infusion devices. The connectors would tend to be less adversely affected by twisting or rotating forces while coupled to electrical connection ports in the infusion devices. Such functionality can be advantageously provided in a relatively compact, robust, and easy to install electrical connector with associated microcontroller software as will be described by example herein.

Figure 1:
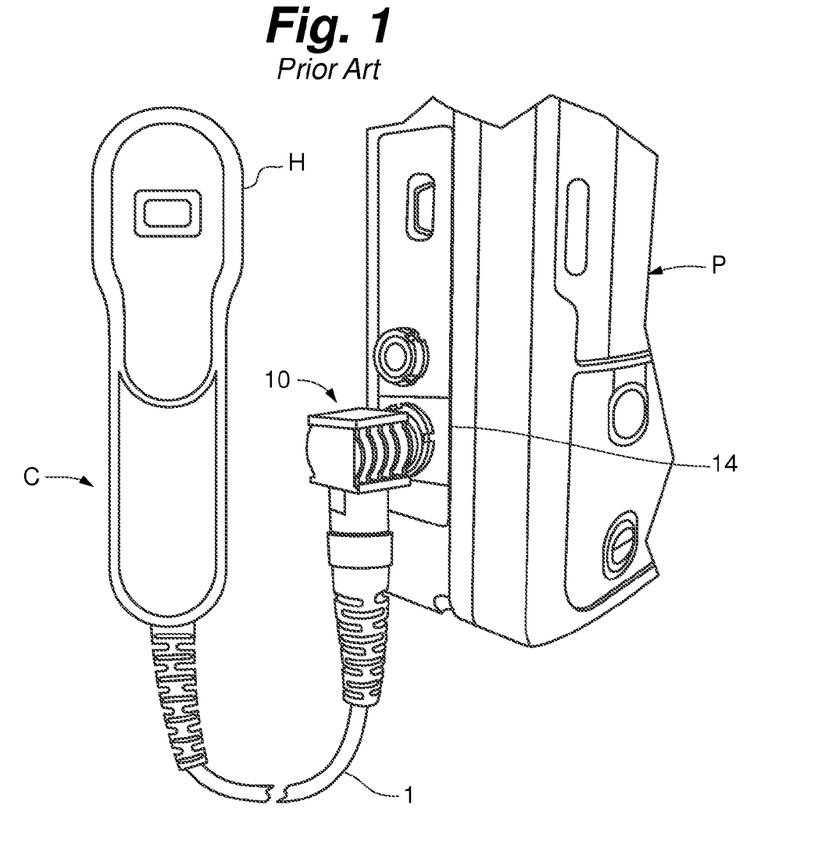
FIG. 1 is an illustration of an example of a remote dose cord of the prior art with a hand-held controller, connected to an infusion device.
Figure 1A:
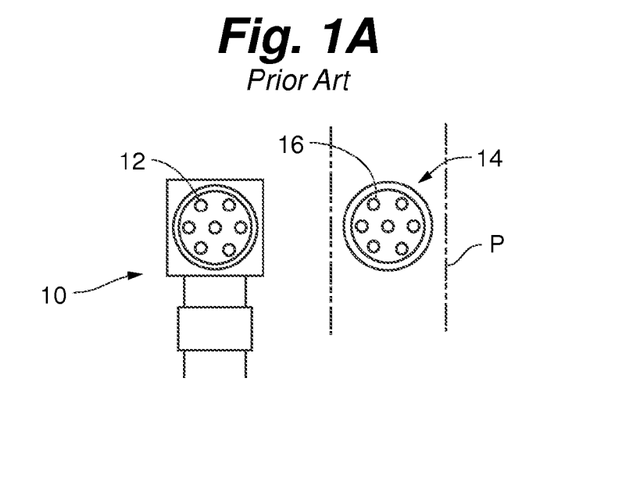
FIG. 1A is a front view of mating connectors of the remote dose cord and the infusion device, as illustrated in FIG. 1.

Referring now to FIGS. 1 and 1A, therein illustrated is an example of a remote dose cord C of the prior art, having a hand-held controller H that is connected to an infusion device such as an ambulatory infusion pump P. In particular, cord C is illustrated as being electrically connected to pump P by way of an electrically-conductive, insulated electrical transmission cord or cable 1 terminating in a conventional electrical connector 10 having pins 12 (visible in FIG. 1A). Connector 10, in turn, engages an electrical connection port 14 on the pump having sockets 16 (visible in FIG. 1A) corresponding to pins 12 of connector 10. The aforementioned problems in use of such a connector may be readily apparent with reference to the drawings, since any twisting or rotating forces applied to connector 10 would tend to shear, deform, or otherwise break one or more pins 12 residing in sockets 16 of port 14.

Figure 2:
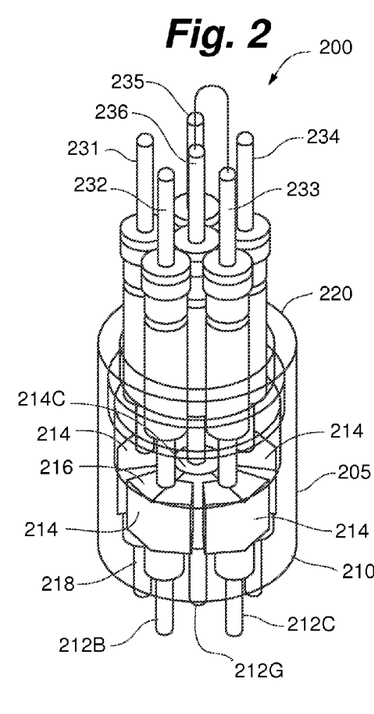
FIG. 2 is an illustration of an example of a rotatable electrical connector.
Figure 2A:
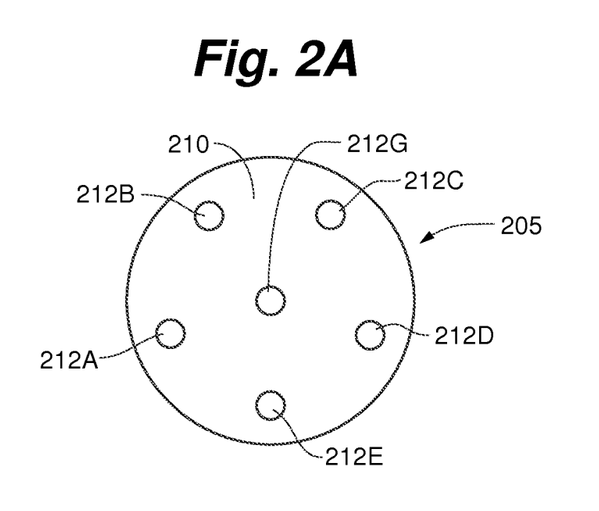
FIG. 2A is a bottom view of the example of the rotatable electrical connector shown in FIG. 2.

Referring now to FIG. 2, therein illustrated is an example of an embodiment of a rotatable electrical connector 200. In this example of connector 200, a base housing 205 has a bottom surface 210. A top housing 220 is rotatably engaged with base housing 205. A plurality of contact pads 214 are arranged radially within base housing 205. This example of connector 200 includes five contact pads 214, with four of them being visible in FIG. 2. Contact pads 214 each have a top surface 216 including symmetrical slopes defining a central, shallow channel therein; and pads 214 each also have a bottom surface 218. With reference to FIGS. 2 and 2A, a plurality of signal pins 212A-E are individually associated with contact pads 214, with each signal pin 212A-E correspondingly projecting outwardly from bottom surface 218 of an associated contact pad 214 and outwardly from bottom surface 210 of base housing 205. This example of connector 200 includes six signal pins: 212A-E, and a ground pin 212G as will be further described. As shown in FIG. 2, a center ground pad 214C is also contained within base housing 205 and has a top surface and a bottom surface. As shown in FIGS. 2 and 2A, ground pin 212G projects outwardly from the bottom surface of center ground pad 214C and outwardly from bottom surface 210 of base housing 205. A plurality of conductors 231-235 are arranged radially within top housing 220, and individually correspond to contact pads 214 upon which they are located at a given time within base housing 205. Each conductor 231-235 has a bottom surface that is capable of being in rotatable contact with top surface 216 of each contact pad 214. Each conductor 231-235 also has a top surface that projects outwardly from top housing 220. Finally in connector 200, a ground conductor 236 is centrally located within top housing 220 and is surrounded by conductors 231-235. Ground conductor 236 is spatially stationary, since it is only intended to rotate about its own longitudinal axis as will be described; but it has a bottom surface that is in rotatable electrical contact with the top surface of center ground pad 214C in base housing 205. Ground conductor 236 also has a top surface that projects outwardly from top housing 220. In this example, conductor 233 is "common" to (or, grounded with) ground conductor 236 to serve as an "index" as will be further described. In FIGS. 2 and 2B-D, this common grounding between conductors 233 and 236 is indicated by a line connecting the top surfaces of the two conductors. As will also be further described, each conductor 231-236 has a defined function in operation with a remote dose cord and an infusion system.

Although not illustrated, it is to be understood in this example of connector 200 that conductors 231-235 are "spring loaded" or are engaged with spring-type components—or they may inherently or internally possess spring or elastic-type properties—which would allow them to move and be displaced slightly vertically in the drawings. Such vertical spring-type action of each conductor 231-235 permits movement, clockwise or counterclockwise, of the shallow channels in top surfaces 216 of contact pads 214 as shown into positive engagement with other conductors when top housing 220 and base housing 205 are twisted or rotated with respect to each other as will be further described. It is to be appreciated that the aforedescribed symmetrical slopes in top surfaces 216 of contact pads 214—which define the central, shallow channels therein—provide a detent or "click stop positioning" for verifying and ensuring positive engagement of each conductor 231-235 as they move into new positions relative to contact pads 214 subsequent to rotation between housings 205 and 220. It is also to be appreciated and understood that in this example of rotatable electrical connector 200, ground pin 212G, center ground pad 214C, ground conductor 236, and index conductor 233 are commonly connected to ground. As housings 220 and 205 rotate with respect to each other, index conductor 233 rotates circumferentially around a common longitudinal or vertical axis of ground pin 212G, center ground pad 214C, and ground conductor 236.

Figure 2B:
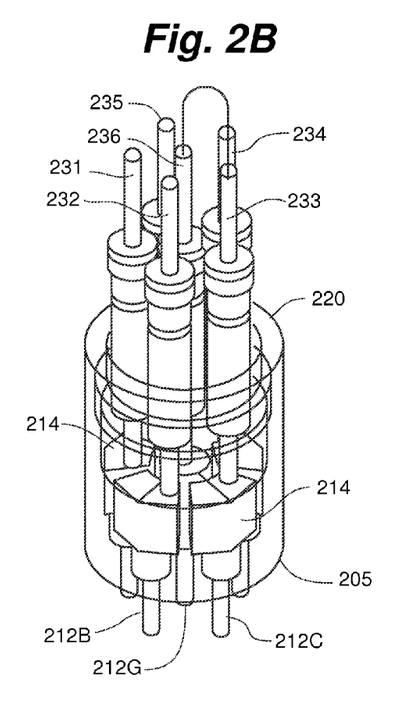
FIG. 2B is an illustration of the example of the rotatable electrical connector of FIG. 2, shown in initial rotation.
Figure 2C:
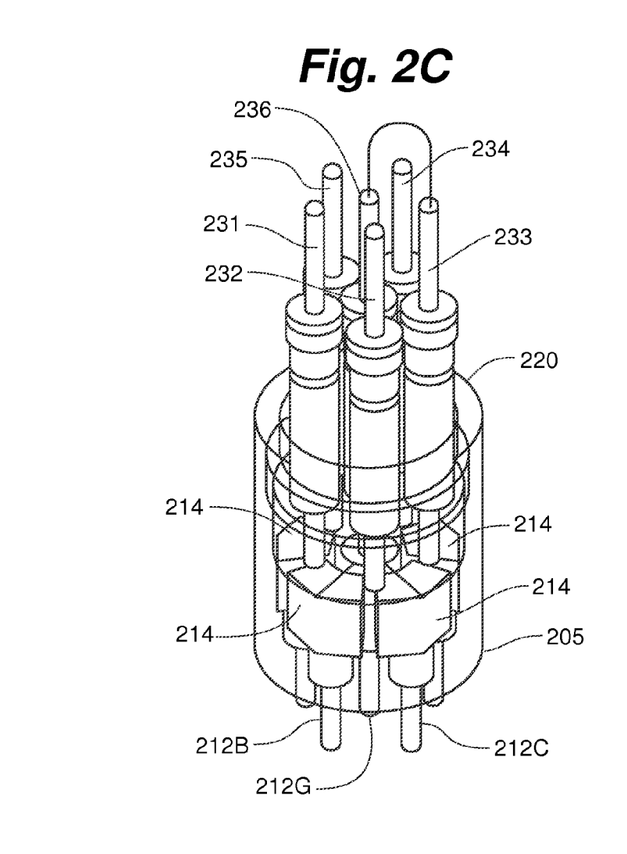
FIG. 2C is an illustration of the example of the rotatable electrical connector of FIGS. 2 and 2B, shown in a further rotation.
Figure 2D:
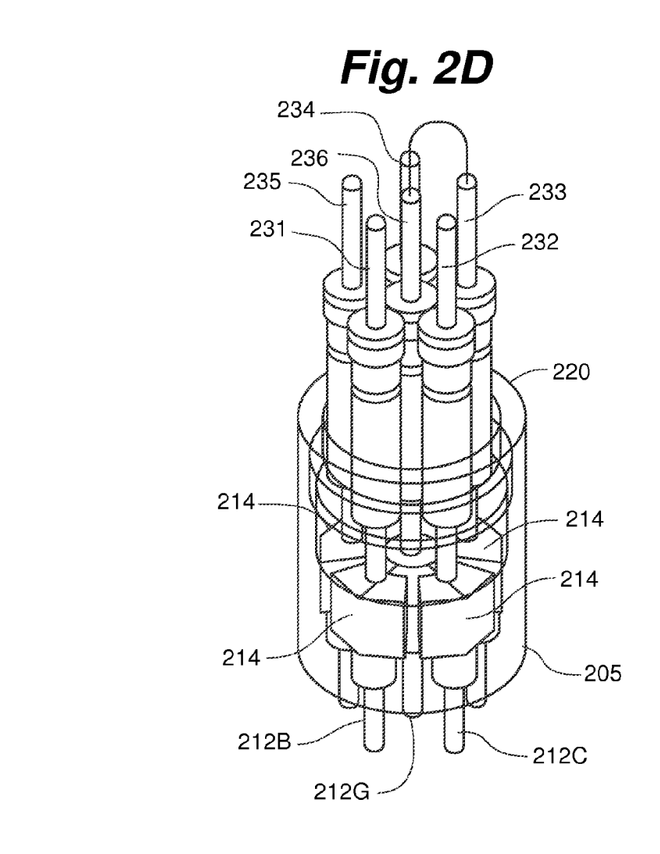
FIG. 2D is an illustration of the example of the rotatable electrical connector of FIG. 2, shown after rotation in FIGS. 2B-C.

With reference to FIGS. 2-2D, it is to be understood in this example that, although not illustrated, conductors 231-235 and ground conductor 236 can be "hard" wired or be electrically coupled permanently to corresponding connections in an electrically-conductive, insulated electrical transmission cord or cable extending from a hand-held controller of a remote dose cord as aforedescribed. Also although not illustrated, in this example of FIGS. 2-2D and the corresponding FIG. 3, it is to be understood that pins 212A-E and G would be plugged into corresponding sockets in an electrical connection port of an infusion device as aforementioned. Also as aforementioned, conductors 231-236 each have a defined, dedicated function in operation with a remote dose cord and an infusion device. For example, in a six-conductor device such as shown in FIGS. 2-2D: conductor 231 serves as a normally open switch; conductor 232 provides power to a blue LED in the hand-held controller; conductor 233 serves as a normally closed switch or index as aforementioned; conductor 234 provides power to the remote dose cord; conductor 235 provides power to a red LED in the hand-held controller; and conductor 236 is grounded with index conductor 233 as aforementioned.

Figure 3:
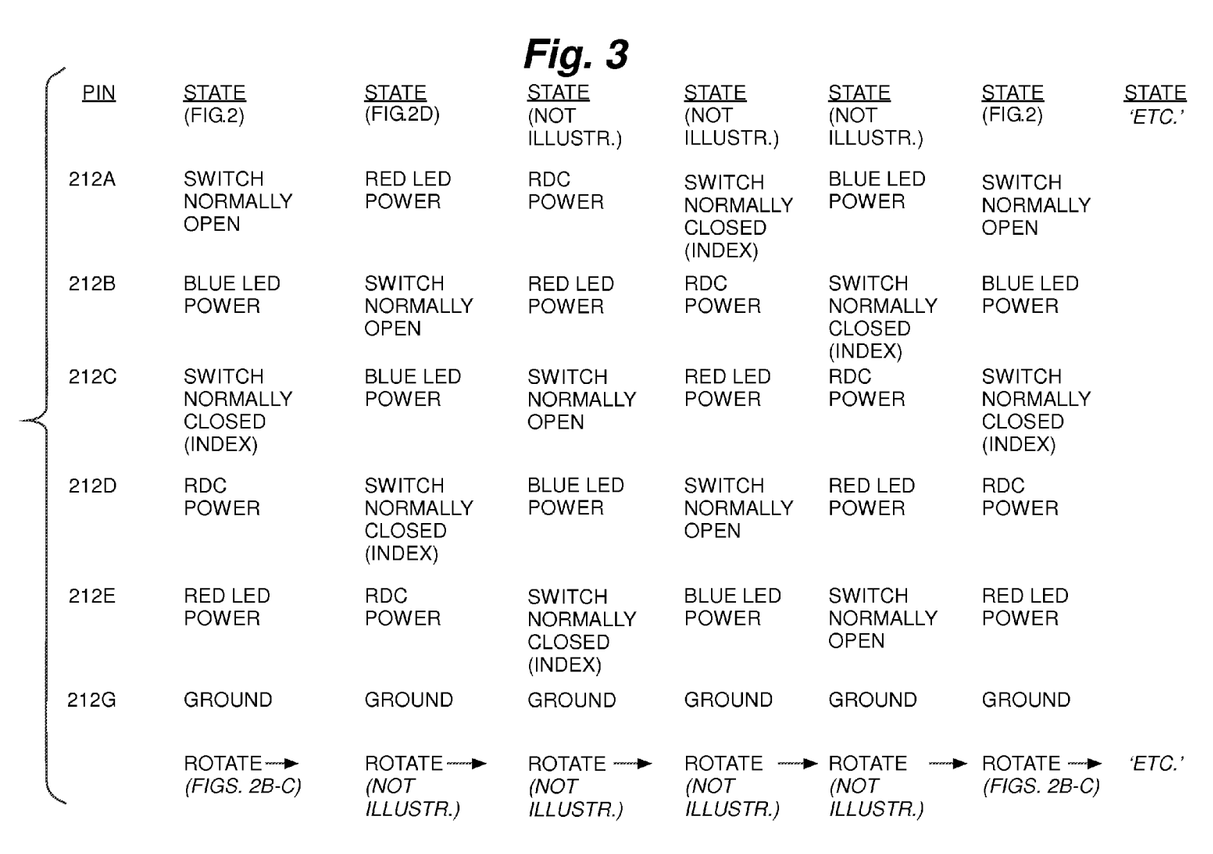
FIG. 3 is a table illustrating an example of operation of the example of the rotatable electrical connector of FIGS. 2-2D.

In non-rotatable devices, such as in known connectors, the pins would normally be in alignment with—and in fact would usually be connected directly and physically to—the conductors, or the pins would simply be "hard wired" to corresponding electrical wires in the dose cord itself. However, in a rotatable connector as described by example or otherwise contemplated herein, pins 212 would not be so dedicated to one function (except for center ground pin 212G which would remain grounded as aforementioned); that is, as housings 205 and 220 are twisted or rotated relative to each other, conductors 231-235 come to rest in the central channels on top surfaces 216 of particular pads 214 depending on their circular distance of travel while housings 205 and 22 are being rotated. FIG. 3 is thus a table which illustrates operation of connector 200 in use with a medical infusion device.

FIG. 3 shows a sequence of states of pins 212A-E, as top housing 220 of connector 200 is shown as being rotated counterclockwise in FIGS. 2, 2B, 2C, and 2D relative to base housing 205. In this example of use of a rotatable electrical connector 200, although not specifically illustrated, conductors 231-236 are electrically coupled or wired to a remote dose cord, and signal pins 212A-E along with ground pin 212G are removably coupled to a mating socket of an infusion device. As housing 220 rotates one full position counter-clockwise relative to base housing 205, a microcontroller and associated software in the infusion device (not illustrated) notes a change of electrical connection of index conductor 233 from pin 212C to pin 212D through their corresponding pads 214. Thus, as so indexed, pins 212A-E may be "remapped" as shown in FIG. 3 via the software and the microcontroller. For example, in FIG. 3 with reference to FIG. 2, pin 212B is shown as being associated (via corresponding pad 214) with conductor 232 that is dedicated to "Blue LED Power" in the hand-held controller of the remote dose cord. As housing 220 rotates one full position counter-clockwise relative to base housing 205 as shown in FIGS. 2B-D, conductor 232 (which is dedicated to "Blue LED Power" as aforementioned) becomes electrically disconnected from pin 212B and instead becomes electrically connected to pin 212C through a corresponding pad 214. The software then, as shown in FIG. 3, remaps pins 212A-E such that pin 212C now becomes associated with "Blue LED Power."

It is to be appreciated and understood that any clockwise or counter-clockwise rotation of housing 220 relative to housing 205 would result in the aforedescribed remapping of the pins, relative to the index conductor and pin to which the index conductor becomes electrically connected, thereby providing a rotatable electrical connection between a remote dose cord and an infusion device.

It is also to be appreciated and understood that types, components, dimensions, fabrication processes, and other particulars and parameters of aforedescribed example embodiments can be substituted for others as desired, or that accessories can be added thereto. For example, an ambulatory infusion pump can comprise a "CADD®-Solis VIP ambulatory infusion system" with a remote dose cord, each being commercially available from Smiths Medical ASD, Inc. The remote dose cord could advantageously include a rotatable electrical connector such as the example connector 200 as aforedescribed.

Irrespective of a particular embodiment, it is to be appreciated and understood that embodiments of a rotatable electrical connector—as disclosed by example or otherwise contemplated herein—can be characterized in that: the top housing and the plurality of conductors rotate relative to the base housing and the plurality of signal pins; and a microcontroller remaps the pins according to rotation of the top housing with respect to one of the plurality of conductors that is electrically connected to the ground conductor.

Furthermore, and again irrespective of a particular embodiment, it is to be appreciated and understood that embodiments of a rotatable electrical connector—as disclosed by example or otherwise contemplated herein—can be characterized in that the plurality of signal pins are removably coupled to an infusion device.

It is also to be appreciated and understood that in another embodiment, although not illustrated in the drawings, a selected pair of the plurality of conductors can be electrically connected to thereby create a rotational index among the remaining plurality of conductors. In such an embodiment, therefore, a ground pad, a ground pin, and a ground conductor might possibly be omitted.

While rotatable electrical connectors have been particularly shown and described with reference to the accompanying figures and specification, it should be understood however that other modifications thereto are of course possible; and all of them are intended to be within the true spirit and scope of novel and inventive devices described herein. Thus, configurations and designs of various features could be modified or altered depending upon particular embodiments. For example, FIG. 1A illustrates a 7-pin arrangement while FIGS. 2-2C illustrate 6-pin arrangements; but any number of pins may be provided in a rotatable electrical connector as described by example or otherwise contemplated herein. Furthermore, for example, the aforementioned detents or provision of "click stop positioning" between the conductors and the contact pads could be omitted in a particular embodiment.

Regardless of particular components or modes of action, it is to be appreciated and understood that rotatable electrical connectors such as have been described by example or otherwise contemplated herein provide coupling of remote dose cords to medical infusion devices while not being adversely affected by twisting or rotating forces as aforementioned. It is also to be appreciated and understood, as aforementioned, that the connectors can comprise relatively compact, robust, and easy to install devices.

It is also to be appreciated and understood that rotatable electrical connectors, such as have been described by example or otherwise contemplated herein, may advantageously provide relatively easy and ergonomic connections between devices such as, for example, remote dose cords and infusion pumps, since mechanical "keying" of the connections are not of concern when compared to use of known electrical connectors. As such, utilization of these novel and inventive rotatable electrical connectors may be particularly advantageous in, for example, dark or dimly-lighted hospital rooms or with pumps not near eye level.

It is further to be appreciated and understood that rotatable electrical connectors, such as have been described by example or otherwise contemplated herein, may advantageously provide connections between devices other than remote dose cords and infusion pumps. For example, these rotatable electrical connectors may, in particular embodiments, be suitable for serial communication ports (e.g., custom USB, RS-232/485, or Ethernet, etc.) or a "combo port" working for either function.

It is additionally to be appreciated and understood that rotatable electrical connectors, as described by example or otherwise contemplated herein, advantageously might avoid use of mercury (Hg) or other potentially hazardous substances and therefore may be "RoHS compliant" (i.e., in compliance with a "Restriction of Hazardous Substances" directive of the European Union). Moreover, rotatable electrical connectors as described by example or otherwise contemplated herein may be usable in a vacuum and be less susceptible to vibration and external forces than, for example, conventional "slip ring" connectors which may rely on use of electrically conducting substances such as mercury (Hg).

It is further to be understood that dimensioning and scaling of the drawings herein have been chosen to clearly show details of example embodiments. Thus, in some embodiments it is possible that spacing between, or orientations of, various features might be variable and visually different from those illustrated. In any event, dimensioning and scaling could vary significantly across various embodiments of rotatable electrical connectors.

It is additionally to be understood in general that any suitable alternatives may be employed to provide novel and inventive rotatable electrical connectors such as those that are described by example or otherwise contemplated herein.

Lastly, compositions, sizes, and strengths of various aforementioned components of rotatable electrical connectors that are described by example or otherwise contemplated herein are all a matter of design choice depending upon intended uses thereof.

Accordingly, these and other various changes or modifications in form and detail may also be made, without departing from the true spirit and scope of rotatable electrical connectors that may be defined by the appended claims.

What is claimed is:

1. A rotatable electrical connector, comprising:
a base housing having a bottom surface;
a top housing that is rotatably engaged with the base housing;
a plurality of contact pads arranged radially within the base housing, the contact pads each having a top surface and a bottom surface;
a plurality of signal pins individually associated with the plurality of contact pads, with each of the signal pins correspondingly projecting outwardly from the bottom surface of an associated contact pad and outwardly from the bottom surface of the base housing;
a center ground pad within the base housing, the center ground pad having a top surface and a bottom surface;
a ground pin projecting outwardly from the bottom surface of the center ground pad and outwardly from the bottom surface of the base housing;
a plurality of conductors arranged radially within the top housing, the conductors individually corresponding to the plurality of contact pads within the base housing, with each of the conductors having (i) a bottom surface that is capable of being in rotatable contact with the top surface of each of the contact pads and (ii) a top surface projecting outwardly from the top housing; and
a ground conductor centrally located within the top housing and being surrounded by the plurality of conductors, the ground conductor having a bottom surface that is in rotatable contact with the top surface of the center ground pad in the base housing and a top surface projecting outwardly from the top housing.

2. A medical infusion device, comprising:
a rotatable electrical connector of claim 1;
a remote dose cord connected to the plurality of conductors and the ground conductor of the rotatable electrical connector; and
an infusion pump having an electrical connection port, with the plurality of signal pins and the ground pin of the rotatable electrical connector being connected to the electrical connection port of the infusion pump.

3. The rotatable electrical connector of claim 1, characterized in that the top housing and the plurality of conductors rotate relative to the base housing and the plurality of signal pins; and a microcontroller remaps the pins according to rotation of the top housing with respect to one of the plurality of conductors that is electrically connected to the ground conductor.

4. The rotatable electrical connector of claim 3, further characterized in that the plurality of signal pins are removably coupled to an infusion device.

5. A rotatable electrical connector, comprising:
a base housing having a bottom surface;
a top housing that is rotatably engaged with the base housing;
a plurality of contact pads arranged radially within the base housing, the contact pads each having a top surface and a bottom surface;
a plurality of signal pins individually associated with the plurality of contact pads, with each of the signal pins correspondingly projecting outwardly from the bottom surface of an associated contact pad and outwardly from the bottom surface of the base housing; and
a plurality of conductors arranged radially within the top housing, the conductors individually corresponding to the plurality of contact pads within the base housing, with each of the conductors having (i) a bottom surface that is capable of being in rotatable contact with the top surface of each of the contact pads and (ii) a top surface projecting outwardly from the top housing,
wherein a selected pair of the plurality of conductors are electrically connected to thereby create a rotational index among the remaining plurality of conductors.

6. A medical infusion device, comprising:
a rotatable electrical connector of claim 5;
a remote dose cord connected to the plurality of conductors of the rotatable electrical connector; and
an infusion pump having an electrical connection port, with the plurality of signal pins of the rotatable electrical connector being connected to the electrical connection port of the infusion pump.

7. The rotatable electrical connector of claim 5, characterized in that the top housing and the plurality of conductors rotate relative to the base housing and the plurality of signal pins; and a microcontroller remaps the pins according to rotation of the top housing with respect to the selected pair of the plurality of conductors that are electrically connected to create the rotational index.

8. The rotatable electrical connector of claim 7, further characterized in that the plurality of signal pins are removably coupled to an infusion device.

* * * * *